United States Patent
Costantini

(10) Patent No.: US 10,434,157 B2
(45) Date of Patent: Oct. 8, 2019

(54) THERAPEUTIC MULTI-PEPTIDES T SPECIFIC IMMUNE THERAPY FOR TREATMENT OF BRAIN METASTASIS

(71) Applicant: OSE IMMUNOTHERAPEUTICS, Nantes (FR)

(72) Inventor: Dominique Costantini, Paris (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 157 days.

(21) Appl. No.: 15/524,278

(22) PCT Filed: Nov. 6, 2014

(86) PCT No.: PCT/EP2014/073975
§ 371 (c)(1),
(2) Date: May 4, 2017

(87) PCT Pub. No.: WO2016/070928
PCT Pub. Date: May 12, 2016

(65) Prior Publication Data
US 2017/0319672 A1 Nov. 9, 2017

(51) Int. Cl.
*A61K 38/00* (2006.01)
*A61K 39/00* (2006.01)

(52) U.S. Cl.
CPC .......... *A61K 39/0011* (2013.01); *A61K 38/00* (2013.01); *A61K 2039/545* (2013.01); *A61K 2039/55* (2013.01); *A61K 2039/55516* (2013.01); *A61K 2039/55566* (2013.01); *A61K 2039/70* (2013.01)

(58) Field of Classification Search
None
See application file for complete search history.

(56) References Cited

PUBLICATIONS

Barve, M. et al. "Induction of Immune Responses and Clinical Efficacy in a Phase II Trial IDM-2101, a 10-Epitope Cytotoxic T-Lymphocyte Vaccine, in Metastatic Non-Small-Cell Lung Cancer" *Journal of Clinical Oncology*, Sep. 20, 2008, pp. 4418-4425, vol. 26, No. 27.
Beebe, M. et al. "Formulation and characterization of a ten-peptide single-vial vaccine, EP-2101, designed to induce cytotoxic T-lymphocyte responses for cancer immunotherapy" *Human Vaccines*, May 1, 2008, pp. 210-218, vol. 4, No. 3.
Nemunaitis, J. et al. "Phase II Trial of a 10-epitope CTL Vaccine, IDM-2101, in Metastatic NSCLC Patients: Induction of Immune Responses and Clinical Efficacy" *Journal of Immunotherapy*, Nov. 1, 2007, pp. 891-892, vol. 30, No. 8.
Pilla, L. et al. "Multipeptide vaccination in cancer patients" *Expert Opinion on Biological Therapy*, Aug. 1, 2009, pp. 1043-1055, vol. 9, No. 8.
Simmons, O. et al. "Current vaccine updates for lung cancer" *Expert Review of Vaccines*, Jan. 1, 2010, pp. 323-335, vol. 9, No. 3.
Written Opinion in International Application No. PCT/EP2014/073975, dated Jul. 23, 2015, pp. 1-6.

*Primary Examiner* — Sheela J. Huff
(74) *Attorney, Agent, or Firm* — Saliwanchik, Lloyd & Eisenschenk

(57) ABSTRACT

The present invention relates to a peptide vaccine composition OSE-2101 for treatment of brain metastasis in HLA-A2 positive patients.

11 Claims, No Drawings
Specification includes a Sequence Listing.

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Arg Leu Leu Gln Glu Thr Glu Leu Val
1               5

<210> SEQ ID NO 2
<211> LENGTH: 10
<212> TYPE: PRT
<213> ORGANISM: Artificial Sequence
<220> FEATURE:
<223> OTHER INFORMATION: synthetic peptide

<400> SEQUENCE: 2

Tyr Leu Gln Leu Val Phe Gly Ile Glu Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Leu Leu Thr Phe Trp Asn Pro Pro Val
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Lys Val Phe Gly Ser Leu Ala Phe Val
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide
```

-continued

```
<220> FEATURE:
<221> NAME/KEY: MISC_FEATURE
<222> LOCATION: (3)..(3)
<223> OTHER INFORMATION: xaa is alpha-aminobutyric acid

<400> SEQUENCE: 5

Lys Leu Xaa Pro Val Gln Leu Trp Val
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Ser Met Pro Pro Pro Gly Thr Arg Val
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Ile Met Ile Gly His Leu Val Gly Val
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Lys Val Ala Glu Ile Val His Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

Tyr Leu Ser Gly Ala Asp Leu Asn Leu
1               5

<210> SEQ ID NO 10
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is d-alanine
<220> FEATURE:
<221> NAME/KEY: MISC_FEATURE
<222> LOCATION: (3)..(3)
<223> OTHER INFORMATION: Xaa is a cyclohexylalanine
<220> FEATURE:
<221> NAME/KEY: MISC_FEATURE
```

```
<222> LOCATION: (13)..(13)
<223> OTHER INFORMATION: Xaa is d-alanine

<400> SEQUENCE: 10

Xaa Lys Xaa Val Ala Ala Trp Thr Leu Lys Ala Ala Xaa
1               5                   10
```

THERAPEUTIC MULTI-PEPTIDES T SPECIFIC IMMUNE THERAPY FOR TREATMENT OF BRAIN METASTASIS

CROSS-REFERENCE TO RELATED APPLICATION

This application is the U.S. national stage application of International Patent Application No. PCT/EP2014/073975, filed Nov. 6, 2014.

The Sequence Listing for this application is labeled "Seq-List.txt" which was created on Nov. 6, 2014 and is 3 KB. The entire content of the sequence listing is incorporated herein by reference in its entirety.

FIELD OF THE INVENTION

The present invention relates to the field of medicine, in particular of oncology, and more particularly the present invention relates to the treatment of brain metastasis.

BACKGROUND OF THE INVENTION

Among the many undesirable effects of systemic cancer is metastatic spread to the brain, with subsequent deleterious effects on many critical functions controlled by this organ. Brain metastasis (BMs) represents a major health care problem. Common sources of brain metastases are lung, breast, renal and colorectal carcinoma, and malignant melanoma, and it has been estimated that some patients with these cancers may develop brain metastasis in the course of their disease [Langley R R, Fidler I J. *International Journal of Cancer.* 2011; 128(11):2527-2535)]. The incidence of brain metastases from ovarian carcinoma (7/335, 2.1%) was higher than those from uterine corpus carcinoma (4/556, 0.7%), uterine cervix carcinoma (7/1716, 0.4%), and other female genital tract malignancies combined (vagina, vulva, and fallopian tube carcinoma) (0/122, 0%) [Ogawa K, et al. *Neurologia Medico-Chirurgica.* 2008; 48(2):57-62]. The medians of the survival times after diagnosis of brain metastases ranged from 1 to 28 months with a median of the medians of 6.4 months. Thus, overall, the survival of patients after diagnosis of brain metastases from ovarian carcinoma is poor. [Ettie Piura and Benjamin Piura: *Oncol.* 2011; 2011: 527153) 527453]

Metastatic tumors involving the brain overshadow primary brain neoplasms in frequency and are an are important complications in the overall management of a large number of cancers. Among the many primary malignancies, lung, breast, melanoma, renal, and colon cancers are the main causes brain metastases (whereas other cancers such as prostate, liver, bladder, pancreatic, and uterine have a lower propensity to seed the brain). Brain metastases are associated with poor prognosis as well as significant morbidity and treatment is palliative in most cases. Irrespective of the location, origin, and clinical presentation of brain metastases, current therapeutic efforts remain limited to multimodal approaches consisting of symptomatic therapy with corticosteroids, whole brain radiotherapy (WBRT), stereotactic radiosurgery and/or surgery which lead to a median survival of 3 to 6 months. Until today, no effective measures are available to reliably prevent this event. Thus, intense vigilance for relevant symptoms and early confirmation of brain metastases is critical to enable intervention and to minimize irreversible damage of the nervous system. The lack of clinically or biologically-based targeted therapies is mainly due to the few conceptual frameworks and even fewer in vitro and in vivo model systems for studying brain metastases.

The brain is one of the most common sites for lung adenocarcinoma metastasis [Sperduto P W, et al. *J Clin Oncol* 2012; 30:419-25]. These patients have poor median survival, and more effective therapies are urgently required. Since traditional chemotherapy is less effective against metastatic brain tumors, radiotherapy remains the main therapeutic or palliative option for inoperable central nervous system (CNS) disease. Radiotherapy supplemented with steroids has yielded responses rates of 50-75% for intracranial lesions, providing rapid attenuation of neurologic symptoms and improvement of performance status However, brain metastases still herald a poor prognosis with a median survival of less than six months. Patients with advanced NSCLC (non-small-cell lung carcinoma) relapsing after chemotherapy generally have a poor prognosis, particularly in the case of patients having brain metastases.

Brain metastases are a common problem in patients with metastatic NSCLC. About 7%-10% of NSCLC patients present with brain metastases at the time of initial diagnosis, and a significant number of patients develop brain metastases at some point during their illness.

Medical treatment directed at cancer cells that have seeded into the brain is ineffective. The failure of chemical therapy has always been attributed to an intact Brain Blood Barrier and the acquisition of drug resistance by the cancer cells.

Standard treatment for NSCLC's brain metastases is Whole brain radiation therapy (WBRT). With this treatment (treatment schedule of 30 Gy), median survival is 3-6 months depending on number of lesions, their radiosensitivity, and the status of systemic disease (Tse V, Brain Metastasis Treatment & Management-Medscape Updated: Apr. 16, 2014).

More aggressive treatment with surgery or stereotactic radiotherapy is possible only in a subset of patients (these modalities have many limitations depending on the location and characteristics of the tumor). The role of systemic treatment in this setting remains controversial. Data from large series of patients (treated for example with gefitinib, see below) are lacking because the presence of brain metastases disease has mostly been considered among exclusion criteria, and, usually, data on brain metastases are not analyzed separately.

Classical medical treatment directed at cancer cells that have seeded into the brain are mostly ineffective. The failure of chemical therapy has always been attributed to an intact blood brain barrier (BBB) and by the acquisition of drug resistance by cancer cells. Most tumors that metastasize to the brain are not chemosensitive. A variety of chemotherapeutic agents have been used to treat brain metastasis from lung, breast, and melanoma, including cisplatin, cyclophosphamide, etoposide, teniposide, mitomycin, irinotecan, vinorelbine, etoposide, ifosfamide, temozolomide, fluorouracil (5FU), and prednisone. In most cases, 2-3 of these agents are used in combination and in conjunction with WBRT. Unfortunately, the outcome with this approach is not promising.

The advent in small-molecule tyrosine kinase inhibitors (TKI has helped to transform the management of brain metastasis. Gefitinib and erlotinib, epidermal growth factor receptor (EGFR) TKI, have shown promising results in treating NSCLC that metastasize to the brain. But these treatments are mainly efficient with patients with the EGFR mutation (Ceresoli G L et al. (2004) *Ann Oncol.* 15(7): 1042-7.

Monoclonal antibodies such as trastuzumab have been used in treating metastatic breast cancer. The latter, however, is not that effective in crossing the BBB and results in relapse within the central nervous system.

Therefore, there is still a strong need of therapy in order to treat brain metastases and offer a longer survival than the usual 3 to 6 months.

SUMMARY OF THE INVENTION

The object of the present invention relates to a new treatment of brain metastases. This treatment relies on the use of a combination of 10 peptides (called herein OSE-2101) as a peptide T specific cancer immunotherapy for brain metastases. The inventors surprisingly discovered that, despite the BBB and a poor prognosis for such a disease, treatment of patients with brain metastases with OSE-2101 is associated with a much longer overall survival than expected as well as a much longer time without disease progression.

Accordingly, the present invention relates to OSE-2101 composition, a multi-epitope T specific cancer immunotherapy, for use in the treatment of brain metastases, in particular in an HLA-A2 positive patient. It also relates to the use of the OSE-2101 composition for the manufacture of a multi-epitope T specific cancer immunotherapy for the treatment of brain metastases, in particular in an HLA-A2 positive patient. It further relates to a method for treating brain metastases in an HLA-A2 positive patient, comprising the administration of a therapeutic effective amount of OSE-2101 composition, a multi-epitope T specific cancer immunotherapy.

The OSE-2101 composition comprises the following optimized epitopes or small peptides RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMP-PPGTRV (SEQ ID No 6), IMIGHLVGV (SEQ ID No 7), KVAEIVHFL (SEQ ID No 8), YLSGADLNL (SEQ ID No 9), aKXVAAWTLKAAa (SEQ ID No 10, with X and a respectively indicating cyclohexylalanine and d-alanine).

Preferably, the brain metastasis originates from a cancer selected from the group consisting of: lung cancers (i.e., NSCLC non-small cell lung cancer and small cell lung cancer), mesothelioma, breast cancers, melanoma, ovarian, head and neck, colon, gastro-intestinal, lymphoma, leukemia, uterine carcinoma, especially uterine corpus and/or uterine cervix carcinoma, testicular or renal cancers. More preferably, the brain metastasis originates from NSCLC.

In a preferred embodiment, the patient is HTL (Helper T Cell) positive.

In particular, the patient may have already received several lines of treatment prior to the treatment, i.e. by OSE-2101 composition.

Preferably, the treatment is administered parentally, preferably subcutaneously.

In a particular embodiment, the small peptides are emulsified in incomplete Freund's adjuvant or the like, preferably Montanide ISA-51. Preferably, the doses of peptide are ranging from 0.1 to 10 mg of peptide per injection dose. More preferably, the total peptide dose for each injection is 5.0 mg.

In a particular embodiment, the peptides combination is administered every two-eight weeks for at least four to six injections. More specifically, the peptides are administered every three weeks for the first 15 weeks, then every 2 months for one year, and then quarterly for two years.

DETAILED DESCRIPTION OF THE INVENTION

The present invention relates to a new therapy of brain metastases based on the OSE-2101 multi-epitope T specific cancer immunotherapy. Surprisingly, the inventors have demonstrated that a peptide multi-epitopes combination gives unexpected survival results in brain metastases treatment. Until then, it was thought that, because of the BBB and the seriousness of brain metastases disease, the production of an immune response in the brain would be ineffective or, at least, that, unless some extraordinary discovery was made, immune-based therapies would not be effective if not combined with other modalities targeting critical aspects of cancer biology (Lishenge Ge et al, Clinical and developmental Immunology, 2010: 296453). On the contrary, the inventors have discovered, not only that a multi-epitope T specific cancer immunotherapy can be effective on brain metastases, but that OSE-2101 as a peptide T specific cancer immunotherapy gives, by itself, greater results than the known treatments. The OSE-2101 multi-epitope T specific cancer immunotherapy is otherwise related to an intriguing immune mechanism of action based on CTL activity and, surprisingly, an HTL response too.

Definitions

An "epitope" is the collective features of a molecule, such as primary, secondary and tertiary peptide structure, and charge, that together form a site recognized by an immunoglobulin, T cell receptor or HLA molecule. Alternatively, an epitope can be defined as a set of amino acid residues which is involved in recognition by a particular immunoglobulin, or in the context of T cells, those residues necessary for recognition by T cell receptor proteins and/or Major Histocompatibility Complex (MHC) receptors. Epitopes are present in nature, and can be isolated, purified or otherwise prepared or derived by humans. For example, epitopes can be prepared by isolation from a natural source, or they can be synthesized in accordance with standard protocols in the art. Throughout this disclosure, epitopes may be referred in some cases as peptides or peptide epitopes.

"Human Leukocyte Antigen" or "HLA" is a human class I or class II Major Histocompatibility Complex (MHC) protein (see, e.g., Stites, et al., IMMUNOLOGY, 8$^{TH}$ ED., Lange Publishing, Los Altos, Calif. (1994). HLA molecules are grouped on the basis of shared peptide-binding specificities. For example, HLA-A2 is a particular type of HLA molecules which share similar binding affinity for peptides bearing certain amino acid motifs. The methods for determining the HLA-A2 status in a patient are well-known and easy to obtain (i.e. serological samples) by the one skilled in the art.

A "peptide epitope" is a peptide that comprises an allele-specific motif or supermotif such that the peptide will bind an HLA molecule and induce a CTL and/or HTL response. Thus, peptide epitopes of the invention are capable of binding to an appropriate HLA-A2 molecule and thereafter inducing a cytotoxic T lymphocyte (CTL) response, or a helper T lymphocyte (HTL) response, to the peptide.

A "PanDR peptide" or "PADRE®" peptide is a member of a family of molecules that binds more than one HLA class II molecule. The pattern that defines the PADRE® family of molecules can be referred to as an HLA Class II supermotif. A PADRE® molecule binds to HLA class II molecules and stimulates in vitro and in vivo human HTL responses. PADRE peptides are described in the patent EP735893.

A "CTL and/or an HTL response" is a protective or therapeutic immune response to an antigen derived from a pathogenic antigen (e.g., an antigen from an infectious agent or a tumor antigen), which in some way prevents or at least partially arrests disease symptoms, side effects or progression. The immune response may also include an antibody response which has been facilitated by the stimulation of helper T cells.

The staging of a cancer describes the severity of a person's cancer based on the size and/or extent (reach) of the original (primary) tumor and whether or not cancer has spread in the body (metastasis). NSCLC stages are numbered from 0 to IV. Stages I IIb and IV are the most advanced stages.

"ECOG (Eastern Cooperative Oncology Group) Performance Status" are used by doctors and researchers to assess how a patient's disease is progressing and assess how the disease affects the daily living abilities of the patient. ECOG Performance Status are numbered from 0 to 5. A performance status of 0 match to patients who are fully active and able to carry on all pre-disease performance without restriction. A performance status of 1 match to patients who are restricted in physically strenuous activity but ambulatory and able to carry out work of a light or sedentary nature, e.g., light house work, office work.

The term "overall survival" (OS) refers to the length of time from the date of the start of treatment that patients are still alive. In a clinical trial, measuring the overall survival is one way to see how well a new treatment works.

Multi-Epitopes T Specific Cancer Immunotherapy

Multi-epitopes T specific cancer immunotherapy is able to help the immune system to develop immune memory that can have long-lasting, tumor-specific effects. Peptide epitopes have been used for the induction of cytotoxic T-lymphocyte (CTL) responses in patients with cancer, in numerous clinical studies, with some encouraging overall results. However, survival specific results have not been reported in brain metastases. Indeed, due to the relative isolation of brain from the systemic circulation mainly due to the BBB, the initiation of productive immune responses in the brain appears to be much more limited than with other types of cancers. Even if local microglial cells can process and present tumor-associated antigens to T lymphocytes, few naive T cells normally transit into the brain.

An effective peptide T specific cancer immunotherapy requires induction of a wide breadth of CTL specificities. This can be best achieved with optimized epitopes targeting multiple Tumor Associated Antigens (TAAs) as a multi-epitopes combination targeting at least 5 tumor antigens and based on epitopes combination. The original combination used here (OSE-2101) is made by wild-type epitopes and modified epitopes (heteroclitic and fixed anchors epitopes). More detailed information on heteroclitic and fixed anchors epitopes can be found for instance in the patent EP1620456.

OSE-2101 is a multi-epitope T specific cancer immunotherapy composed of 10 synthetic peptides. Nine of the peptides have been designed to induce a CTL response against TAAs. More particularly, the T specific immune therapy is designed for administration to patients for the induction of CTL directed against carcinoembryonic antigen (CEA), p53, human epidermal receptor-2/neurological (HER-2/neu) and melanoma antigen 2 and 3 (MAGE-2/3). These TAAs have been chosen based on epidemiology because they are frequently over-expressed in various advanced cancers as colon cancers, ovarian cancers, breast cancers and NSCLC. Each CTL epitope is restricted by HLA-A2 superfamily of major histocompatibility complex class I molecules, thereby providing coverage of approximately 45% of the general population. The tenth synthetic peptide is the pan-DR epitope (PADRE), a rationally designed helper T-lymphocyte (HTL) epitope included only to increase the magnitude of CTL responses.

OSE-2101 composition comprises or consists of the following peptides:
RLLQETELV SEQ ID No 1
YLQLVFGIEV SEQ ID No 2
LLTFWNPPV SEQ ID No 3
KVFGSLAFV SEQ ID No 4
KLBPVQLWV SEQ ID No 5, with B indicating α-aminoisobutyric acid
SMPPPGTRV SEQ ID No 6
IMIGHLVGV SEQ ID No 7
KVAEIVHFL SEQ ID No 8
YLSGADLNL SEQ ID No 9
aKXVAAWTLKAAa SEQ ID No 10, with X and a respectively indicating cyclohexylalanine and d-alanine.

The peptides can be synthesized using standard Boc or Fmoc chemistry for solid phase peptide synthesis starting with the appropriate resin, and purified by standard methods. Alternatively, the peptide may be produced by genetic engineering with recombinant cells or by RNA, for instance by in vitro translation system.

The OSE-2101 composition may comprise a pharmaceutically acceptable carrier or excipient. More preferably, the pharmaceutically acceptable carrier is an aqueous carrier, especially a buffer. In particular, it may comprise one or several adjuvants. For instance, adjuvants can be incomplete Freund's adjuvant, mineral oil adjuvant, aluminum hydroxide, or alum, GM-CSF. Other suitable adjuvants are well-known in the art.

In one embodiment, the OSE-2101 T specific cancer immunotherapy may comprise peptide pulsed antigen presenting cells, such as dendritic cells.

Preferably, in the OSE-2101 composition, the peptides are emulsified in incomplete Freund's adjuvant or the like. In a preferred embodiment, the adjuvant is a mineral oil adjuvant, similar to Incomplete Freund's Adjuvant, manufactured and supplied by Seppic S A, Paris, FRANCE. In a most preferred embodiment, the adjuvant is Montanide® ISA 51.

Each peptide of the composition can be present at a concentration of 0.1 mg/ml to 1 mg/ml, preferably 0.5 mg/ml. Preferably, all the peptides are present in the composition at the same concentration.

Preferably, OSE-2101 composition is a sterile, preservative-free emulsion of the 10 peptides at a concentration of 0.5 mg/ml each, formulated in Montanide® ISA 51 adjuvant at a ratio of 1:1 (w:w) and filled into rubber-stoppered glass vials, and refrigerated at 2° to 8° C.

OSE-2101 is manufactured under aseptic conditions. Peptides are dissolved in three different solvents, sterile filtered, pooled and then emulsified in adjuvant via homogenization under controlled conditions. Product release testing included appearance, endotoxin, sterility, viscosity, particle size, peptide concentration of each peptide, volume, pH and potency. Preparation of OSE-2101 composition is detailed in WO2004/094454, FIG. 3A and pages 105-106, the disclosure of which being incorporated herein by reference.

Optionally, in addition to the 10 peptides of OSE-2101, the peptide composition of the present invention may further comprise additional peptides, in particular peptide epitopes used for inducing of cytotoxic T-lymphocyte (CTL) responses and targeting TAAs.

Brain Metastases:

Brain metastases are a common type of intra-cranial neoplasm. Of the many primary malignancies, lung, breast, melanoma, renal, and colon cancers are the main sources for brain metastases. About half of metastatic brain tumors are from lung cancer. Brain metastases can also occur after ovarian, head and neck, mesothelioma, gastro-intestinal, sarcoma, germ cell tumors, kidney cancers, uterine carcinoma, especially uterine corpus and/or uterine cervix carcinoma, leukemia, lymphoma, breast cancers and bladder cancers. Primary brain tumors may spread to other parts of the brain (metastasis or to the spine).

According to a preferred aspect of the present invention, subjects of treatment with OSE-2101 composition are patients with brain metastases and are HLA-A2 positive. In a preferred embodiment, patient's brain metastases are due to one of the following cancers: lung, breast, melanoma, renal, colon, ovarian, uterine carcinoma, especially uterine corpus and/or uterine cervix carcinoma, head and neck, bladder, mesothelioma, gastro-intestinal, sarcoma, germ cell tumors, leukemia, lymphoma, and brain cancers. Preferably, the patient has a lung cancer, in particular a NSCLC. Optionally, the patient has already received several lines of treatment prior to the vaccination. In a particular embodiment, the patient has a positive HTL response.

Defects in human leukocyte antigen class I antigen (HLA-A2) processing machinery (APM) component expression can have a negative impact on the clinical course of tumors and the response to T cell-based immunotherapy. Comparison of unpaired 50 primary cancers and 33 brain metastases showed lower expression of β2-microglobulin, transporter associated with antigen processing and immune reactions in the brain lesions, [Liu Y, et al, *Cancer Immunol Immunother.* 2012 June; 61(6):789-801]. β2 microglobulin is an important component of MHC class I molecules as HLA-A2 and is necessary for cell surface expression of MHC class I and stability of the peptide binding groove.

It is therefore surprising to achieve a T cell response and a clinical response in the case of such advanced brain metastasis patients as observed by the inventors when a defect of HLA A2 machinery is well described.

It further relates to a method for treating brain metastases in an HLA-A2 positive patient, comprising the administration of a therapeutic effective amount of OSE-2101 T specific immune therapy. The method may further comprise a preliminary step of determining the HLA status of the patient, selecting the HLA-A2 positive patients and administering a therapeutic effective amount of OSE-2101 therapeutic peptides to the HLA-A2 positive patients.

Dosage and Regimen

Within the context of the invention, the term "treatment" or "treating" denotes curative, symptomatic, and preventive treatment. Pharmaceutical compositions and preparations of the invention can be used in humans with existing cancer or tumor, preferably at late stages of progression of the cancer. The pharmaceutical compositions and preparations of the invention will not necessarily cure the patient who has the cancer but will delay or slow the progression or prevent further progression of the disease, ameliorating thereby the patients' condition. In particular, the pharmaceutical compositions and preparations of the invention reduce the development of tumors, and/or prevent metastasis occurrence or development and cancer relapse. In treating the cancer, the pharmaceutical composition of the invention is administered in a therapeutically effective amount.

By "effective amount" it is meant the quantity of the pharmaceutical composition of the invention which prevents, removes or reduces the deleterious effects of brain metastases. It is understood that the administered dose may be adapted by those skilled in the art according to the patient, the pathology, the mode of administration, etc. The dosage and regimen depends on the stage and severity of the disease to be treated, the weight and general state of health of the patient and the judgment of the prescribing physician. More particularly, by "therapeutically efficient amount of the OSE-2101 peptides or composition" is intended the amount which is sufficient to increase the overall survival a patient having brain metastases.

Previous cancer trials have tested escalating doses of peptide, ranging from 0.1 to 10 mg of peptide per injection dose, emulsified in incomplete Freund's adjuvant. At all doses tested, the peptide/incomplete Freund's adjuvant treatment was deemed to be safe and well tolerated, with no severe dose-related systemic toxicities being reported.

OSE-2101 can be administered by any appropriate route, in particular by parenteral route such as subcutaneous, intradermal or intramuscular route or by aerosol, transmucosal, intrapleural, or intrathecal routes. In a most preferred embodiment, the peptides composition is administered subcutaneously. Preferably, OSE-2101 is designed for subcutaneous injection.

In a preferred embodiment, the total peptide dose for each injection or administration will be 5.0 mg (1 mL of drug product containing 0.5 mg of each peptide).

Preferably, the peptides composition is administered with initial doses followed by boosting doses at established intervals. For instance, the peptides combination can be administered every two-eight weeks for at least four to six injections, more preferably every three-four weeks for at least four to six injections.

Preferably, the peptides combination is administered every three weeks for at least six injections. In another embodiment, the T specific immune therapy is administered every three weeks for the first 15 weeks, then every 2 months through year 1, then quarterly through year 2, for a total of 13 doses.

Optionally, the treatment with OSE-2101 T specific immune therapy can be combined with another cancer treatment. In a preferred embodiment, it is used in combination with a cancer treatment generally used for treating a patient having brain metastases. For instance, the chemotherapy can be selected among cisplatin, cyclophosphamide, etoposide, teniposide, mitomycin, irinotecan, vinorelbine, etoposide, ifosfamide, temozolomide, fluorouracil (5FU), prednisone, tyrosine kinase inhibitors such as gefitinib, erlotinib and crizotinib, and any combination thereof.

HTL Status

The present invention further relates to the use of the HTL status, namely positive or negative, as prognostic marker. Indeed, the inventors surprisingly observed that the patients which are HTL positive presents a longer overall survival. Therefore, HTL-positive status is a prognostic marker of a good overall survival and/or a marker of improved response to a therapeutic multi-epitopes against cancer, in particular a response to the OSE-2101 peptide vaccine.

Further aspects and advantages of this invention will be disclosed in the following experimental section, which should be regarded as illustrative and not limiting the scope of this application.

EXAMPLES

Previous Study of OSE-2101 Vaccination in Patients with HLA-A2 Positive Advanced NSCLC A Phase I I, open-label, multicenter, single dose-group, multiple administration study of OSE-2101 in patients with HLA-A2 positive advanced NSCLC was performed (NCT00104780). Results on CTL immune response and survival were published in the Journal of Clinical Oncology (Barve M, et al, *J Clin Oncol*. September 20; 26(27):4418-25).

Methods and Patients:

The study was designed to evaluate the safety, efficacy (response and survival), and immunogenicity of OSE-2101 in patients with advanced NSCLC who were HLA-A2 positive. The multi-epitope combination was administered subcutaneously at a dose of 5 mg every 3 weeks for the first 15 weeks, then every 2 months through year 1, then quarterly through year 2, for a total of 13 doses.

Patients were to be followed at three months after the last injection. Survival status was then to be ascertained every three months through year three then annually until year five. Tumor staging was performed at baseline with reassessment at weeks 9 and 18 and at months 6, 9, and 12. Leukapheresis was performed before vaccination (at screening) and at weeks 9 and 18 to obtain sufficient cells to conduct the immunogenicity assays. Hematology, electrolytes, liver, other organ functions, urinalysis, and antinuclear antibody titer were assessed. Toxicity was monitored and graded according to the National Cancer Institute Common Toxicity Criteria. All patients signed the protocol-specific local institutional review board approved informed consent form. Response Evaluation Criteria in Solid Tumors were used to evaluate response.

Eligible patients for this study were 18 years or older with histologic confirmation of stage IIIB or IV or recurrent NSCLC. Patients had to have an ECOG performance status of 0 or 1, an absolute granulocyte count $\geq 1,500/\mu L$, platelet count $\geq 100,000/\mu L$, hemoglobin $\geq 10$ g/dL, total bilirubin $\leq 2$ mg/dL, AST (Aspartate Transaminase) and ALT (Alanine Transaminase)$\leq 2.5$ times the upper limit of normal, and serum creatinine $\leq 2$ times the upper limit of normal. Patients with BMs were eligible if the disease was clinically stable for at least 2 months before study entry.

OS (Overall Survival) was estimated using the Kaplan-Meier method. Progression-free survival was to be determined from time of patient registration to date of progression, death or last assessment of tumor response. To measure CTL responses, $2*10^6$ peripheral-blood mononuclear cells (PBMCs)/well (three to four wells per epitope) were stimulated in vitro with each vaccine peptide (10 μg/mL). Ten U/mL of rIL-2 was added after 24 hours. After 10 days of culture, the in vitro-expanded PBMCs were tested for epitope-specific (vaccine CTL epitope and wild-type epitope of vaccine analog) CTL responses, measured by an 18-hour interferon gamma ELISPOT assay.

Immune T cytotoxic response relationship to survival was done by comparing the number of epitopes with measurable enzyme-linked immunosorbent spot assay (ELISPOT) responses in relation to survival using the log-rank statistic.

HTL responses were measured from PBMCs without an in vitro expansion step. PBMCs were thawed, rested overnight in medium, and $2*10^5$ PBMCs/well were stimulated with 10 μg/mL PADRE or irrelevant malaria peptide in the interferon gamma ELISPOT assay.

A total of 135 patients were enrolled, 64 patients were positive for HLA-A2 and 72 patients were HLA-A2 negative. The HLA-A2 negative group was not prospectively observed after determination of negative HLA type, information were only provided for survival. The 64 HLA-A2 positive patients were treated with one or more dose(s) of OSE-2101 and represent the ITT (intention-to-treat) population and the safety population.

The characteristics of the 64 HLA-A2 positive patients were as follows:

Median age: 64 years (26-87 years);
Males: 55%, Females: 45%;
Caucasians: 83%, African Americans: 9%, Asians: 8%.

The majority of patients (43/64, 67%) had Stage I V NSCLC at inclusion. The median number of days since first diagnosis was 416 (range of 74 to 1921 days).

Prior treatment lines for OSE-2101 treated patients were a majority of patients receiving 2 previous lines (65.5%) including a first line with platinum combo:

one previous line: 31% of patients;
two previous lines: 28%;
3 or more previous lines (up to 6 lines): 37.5%.

92% of the treated population had previously received a platinum based chemotherapy and 34% a TKI (gefinitib or erlotinib).

6 patients (9.4%) had received previous radiotherapy for brain metastasis.

18 patients were considered as progressive disease at entry, representing 28% of this treated OSE-2101 population.

The HLA-A2 negative non-treated population demographics were similar to the HLA-A2 positive treated population: 72 patients, a median age of 65 years (33-91 years); 51% of males and 49% of females; 79% of Caucasians. One out of the 72 patients was lost of follow-up.

Results:

In the previous study described above, patients with brain metastases were eligible if the disease was clinically stable for at least 2 months before study entry. 6 patients (9.4% of the NSCLC population of the clinical study) had received previous radiotherapy for brain metastasis. All the 6 patients had a stage IV brain metastases and were entering with a performance status of 1 (see Table 1).

The inventors explored for the first time the effects of the OSE-2101 therapeutic cancer vaccine on these 6 patients presenting brain metastases.

According to the literature, these patients with brain metastases were supposed to have the worse survival time and were thus supposed to be the first to die, shortly in the study.

Surprisingly, these patients achieved a greater long term survival than expected, especially when taking into account the poor prognosis established for these patients who were previously highly treated and were suffering of advanced stage of brain metastases (see Table 1).

These 6 patients with brain metastases were achieving, after receiving the OSE-2101 cancer vaccine, a very long term survival and also a long time without progression (see Table 2). The median OS for patients with brain metastases with a performance status at 1 is described at 4 months in the literature. In the present study, the inventors observed a range of 7 months to 41 months of OS.

Prior the present study, an unresolved question was to know if the multi-epitopes immune therapy was able to by-pass the BBB though induction of T Cytotoxic cells. The evaluation of CTL responses in 5 of the 6 patients shows that each patient had a CTL response to the peptide epitopes of OSE-2101 vaccine. The CTL range was between 1 to 5 CTL epitopes positive responses (see Table 2). Thus, the OSE-2101 therapeutic peptide vaccine is able to by-pass the BBB.

Surprisingly, the study of HTL responses was meaningful. The HTL response is triggered by the pan-DR epitope (PADRE), a rationally designed helper T-lymphocyte epitope. This epitope is traditionally included in multi-epitopes cancer vaccine because it's supposed to slightly improve the magnitude of CTL responses.

In this study, positive HTL patients achieve the longest OS (16.6 months, 24.4 months and 41 months) when compared with negative HTL patients (OS of 9.6 and 11 months). Moreover, disease progression is more rapid with HTL negative patients, compared to HTL positive patients (see Table 2).

The clinical advantage of positive HTL responses has been confirmed with a subset of the patients of the clinical trial. The inventors compared the OS of 18 positive HTL response patients versus 15 negative HTL response patients. The median OS is 744 days (24.3 months) [448 to 980] in HTL positive group whereas the median OS is 520 days (17 months) [214 to 943] in HTL negative group. Then, a difference of 7.4 months is observed.

Conclusion

Brain metastases surprisingly benefit of the therapeutic cancer vaccine OSE-2101 despite the presence of the BBB and the seriousness of the disease at this stage. An important increase of the OS is observed, especially for a poor prognosis population highly previously treated.

Positive HTL responses give surprisingly an OS meaningful clinical advantage. HTL epitope can be used as potency assay due to the OS impact and represent a strong advantage without any in vitro expansion by peptides.

TABLE 1

Patients description

| | Patient Number | | | | | |
|---|---|---|---|---|---|---|
| | 108 NSCLC | 150 NSCLC | 169 NSCLC | 132 NSCLC | 133 NSCLC | 135 NSCLC |
| gender | female | male | male | male | male | male |
| Ethnic origin | caucasian | caucasian | caucasian | caucasian | African american | caucasian |
| age | 46 years | 61 years | 58 years | 79 years | 46 years | 57 years |
| BM Stage | IV | IV | IV | IV | IV | IV |
| ECOG performance status | 1 | 1 | 1 | 1 | 1 | 1 |
| Previous treatments | Radiotherapy (30 GY) and 2 lines of chemotherapy including first line of Cisplatin + VP 16 then CT2103 (paclitaxel polymer) + cisplatine | WBRT (3000 CG-Y) and 2 lines of chemotherapy Carboplatin + taxol ontak | Radiotherapy (30 GY) and 2 lines of chemotherapy carboplatin + taxol then ontak | WBRT (3000 CY) and 3 lines Carboplatine + Taxol Iressa Alimta | Radiotherapy (30 GY) and a first line of Carboplatin + taxol | WBRT (3000 CG-Y) and 3 lines of treatment including a carboplatin + taxotere triapine gemcitabine taxol + carboplatine |

TABLE 2

Patients Survival and Immune responses

| | Patient Number | | | | | |
|---|---|---|---|---|---|---|
| | 108 NSCLC | 150 NSCLC | 169 NSCLC | 132 NSCLC | 133 NSCLC | 135 NSCLC |
| OS | 30.16 months | 41 months[*1] | 16.5 months | 9.6 months | 11 months | 7 months[*2] |
| Time without progression | 11.57 months | 24.39 months[*1] | 11.9 months | 4.53 months | 6.2 months | 2 months[*2] |
| CTL response | 3 epitopes | 2 epitopes | 5 epitopes | 2 epitopes | 1 epitope | Not tested |
| HTL response | + | + | + | − | − | Not tested |

[*1]Patient still alive at the time of the last follow up 41 months,
[*2]treatment stopped after 2 injections for progressive disease.

The analysis of the 6 Brain metastatic patients allows to see a very interesting survival time considering the advanced stage and the poor prognosis of these patients heavily previously treated.

Brain Metastasis (BM) patients (no 108, no 169, no 132, no 133 and no 135) except one (no 150) were entering the trial few weeks after the progression of the cancer though a Brain Metastasis and a radiotherapy.

All BM patients were receiving at least one previous systemic therapeutic line of treatments.

5 patients were entering after at least 2 previous lines of chemotherapy (including first line platinum combo) and 2 patients were receiving 3 previous lines before the T specific immune therapy.

The OSE 2101 treatment was administered subcutaneously every 3 weeks for the 6 first injections (during the induction phase) for all BM patients except one (no 150 receiving 2 injections only). Two patients were entering in the maintenance phase with an injection every 2/3 months (no 108-no 150 both receiving 8 injections).

After radiotherapy as WBRT, median survival of NSCLC described in the literature is 3-6 months with a limited effect on the survival. The evaluation of the median after OSE-2101 treatment in the subgroup of BM patients is at 13 months (range 7 to 41).

The invention claimed is:

1. A method of treating brain metastasis in a HLA-A2 (Human Leukocyte Antigen A2) positive patient comprising: i) selecting a patient having brain metastasis and being HLA-A2 positive; and ii) the administration of a composition comprising T specific immune therapy peptides RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), YLSGADLNL (SEQ ID No 9), and aKXVAAWTLKAAa (SEQ ID No 10, with X and a respectively indicating cyclohexylalanine and d-alanine) to said patient.

2. The method according to claim 1, wherein said brain metastasis originates from a cancer selected from the group consisting of lung cancer, NSCLC non-small cell lung cancer (NSCLC), small cell lung cancer, melanoma, mesothelioma, breast cancers, primary brain cancers, ovarian, uterine carcinoma, especially uterine corpus and/or uterine cervix carcinoma, head and neck, colon, gastro-intestinal, renal cancers, sarcoma, germ cell tumors, leukemia, lymphoma, testicular cancers and bladder cancers.

3. The method according to claim 2, wherein said brain metastasis originates from NSCLC.

4. The method according to claim 1, wherein said patient is HTL (Helper T Cell) positive.

5. The method according to claim 1, wherein the composition is administered parentally.

6. The method according to claim 1, wherein the peptides are emulsified in incomplete Freund's adjuvant, mineral oil adjuvant, aluminum hydroxide, alum, or GM-CSF.

7. The method according to claim 1, wherein the doses of peptide range from 0.1 to 10 mg of peptide per injection dose.

8. The method according to claim 7, wherein the total peptide dose for each injection is 5.0 mg.

9. The method according to claim 1, wherein the composition is administered every two-eight weeks for at least four to six injections.

10. The method according to claim 9, wherein the composition is administered every three weeks for the first 15 weeks, then every 2 months for one year, and then quarterly for two years.

11. The method according to claim 1, wherein said patient has already received several lines of treatment prior to the administration of said composition.

* * * * *

UNITED STATES PATENT AND TRADEMARK OFFICE
CERTIFICATE OF CORRECTION

PATENT NO. : 10,434,157 B2
APPLICATION NO. : 15/524278
DATED : October 8, 2019
INVENTOR(S) : Dominique Costantini It is certified that error appears in the above-identified patent and that said Letters Patent is hereby corrected as shown below:

In the Specification

<u>Column 1,</u>
Line 46, "2011: 527153) 527453]" should read --2011: 527453]--.
Line 48, "and are an are important" should read --and are important--.

<u>Column 5,</u>
Line 15, "Stages I IIb" should read --Stages IIIb--.

<u>Column 9,</u>
Line 5, "Phase I I" should read --Phase II--.

<u>Column 10,</u>
Line 12, "Stage I V" should read --Stage IV--.

Signed and Sealed this
Twenty-sixth Day of November, 2019

Andrei Iancu
*Director of the United States Patent and Trademark Office*